(12) United States Patent
Gafner-Geiser et al.

(10) Patent No.: US 7,914,500 B2
(45) Date of Patent: Mar. 29, 2011

(54) CONTAINER FOR STORING A PRODUCT TO BE INJECTED, AND AN INJECTION DEVICE FOR USE WITH THE CONTAINER

(75) Inventors: Simone Gafner-Geiser, Langenthal (CH); Rudolf Zihlmann, Langnau (CH); Hanspeter Heiniger, Lotzwil (CH)

(73) Assignee: Roche Diagnostics International AG, Steinhausen (CH)

( * ) Notice: Subject to any disclaimer, the term of this patent is extended or adjusted under 35 U.S.C. 154(b) by 570 days.

(21) Appl. No.: 11/564,982

(22) Filed: Nov. 30, 2006

(65) Prior Publication Data

US 2007/0123820 A1    May 31, 2007

Related U.S. Application Data

(63) Continuation of application No. PCT/EP2005/005701, filed on May 27, 2005.

(30) Foreign Application Priority Data

Jun. 2, 2004  (DE) .................. 10 2004 026 805

(51) Int. Cl.
  *A61M 5/32*    (2006.01)
  *A61M 37/00*   (2006.01)
  *A61M 5/20*    (2006.01)
  *A61K 9/22*    (2006.01)

(52) U.S. Cl. ........ 604/192; 604/131; 604/132; 604/135; 604/288.02; 604/891.1; 604/892.1

(58) Field of Classification Search .................. 222/103; 604/131–135, 890.1–892.1, 192
See application file for complete search history.

(56) References Cited

U.S. PATENT DOCUMENTS

| | | | | |
|---|---|---|---|---|
| 4,265,241 | A * | 5/1981 | Portner et al. | 604/131 |
| 5,176,641 | A * | 1/1993 | Idriss | 604/133 |
| 5,346,476 | A | 9/1994 | Elson | |
| 5,383,858 | A | 1/1995 | Reilly et al. | |
| 5,616,132 | A * | 4/1997 | Newman | 604/185 |
| 6,394,981 | B2 * | 5/2002 | Heruth | 604/140 |
| 6,719,739 | B2 * | 4/2004 | Verbeek et al. | 604/288.04 |
| 6,749,587 | B2 * | 6/2004 | Flaherty | 604/151 |
| 7,337,922 | B2 * | 3/2008 | Rake et al. | 222/103 |
| 2002/0052577 | A1 | 5/2002 | Shimazaki | |
| 2002/0177811 | A1 | 11/2002 | Reilly et al. | |
| 2005/0192638 | A1 * | 9/2005 | Gelfand et al. | 607/3 |
| 2007/0207186 | A1 * | 9/2007 | Scanlon et al. | 424/424 |
| 2007/0218298 | A1 * | 9/2007 | Terry | 428/447 |

FOREIGN PATENT DOCUMENTS

DE           272700         4/1914
(Continued)

*Primary Examiner* — Nicholas D Lucchesi
*Assistant Examiner* — Ian K Holloway
(74) *Attorney, Agent, or Firm* — Dinsmore & Shohl, LLP

(57) ABSTRACT

A container for storing a product to be injected, e.g., a therapeutic or diagnostic liquid, wherein the container includes a container body and a piston body arranged in the container body in a sliding manner, the piston body moveable between a rear end position that determines a maximum filling of the container and a front end position to dispense the product, and wherein the container has a maximum opening ratio H/L of approximately 1.25 to 1.0, H corresponding to the maximum height of the container body and L corresponding to the maximum distance between the lateral wall or walls of the container body.

28 Claims, 10 Drawing Sheets

FOREIGN PATENT DOCUMENTS

| | | |
|---|---|---|
| DE | 2108381 | 8/1972 |
| DE | 19652708 | 6/1998 |
| EP | 1028141 A1 | 8/2000 |
| GB | 2107988 A | 5/1983 |
| JP | 6-154322 A | 6/1994 |
| JP | 2001-190665 A | 7/2001 |
| JP | 2002-233572 A | 8/2002 |
| WO | WO 00/02605 | 1/2000 |
| WO | WO 03/026726 A | 4/2003 |

* cited by examiner

CONTAINER FOR STORING A PRODUCT TO BE INJECTED, AND AN INJECTION DEVICE FOR USE WITH THE CONTAINER

CROSS-REFERENCE TO RELATED APPLICATION(S)

This application is a continuation of and claims priority to International Application No. PCT/EP2005/005701, filed on May 27, 2005, which claims priority to German Application No. 10 2004 026 805.3, filed on Jun. 2, 2004, the contents of which are incorporated in their entirety by reference herein.

BACKGROUND

The present invention relates to devices for delivering, administering, dispensing, injecting and infusing substances, and to methods of making and using such devices. More particularly, it relates a container for storing a product to be injected, especially a therapeutic or diagnostic liquid, and to an injection device comprising, incorporating and/or capable of using such a container.

The present invention relates to containers of the type comprising a container body and a piston body, which is arranged in the container body in a sliding manner and which, to dispense the product, can be displaced between a rear end position that determines a maximum filling of the container and a front end position. Containers of this type are used in medical injection devices for storing a therapeutic or diagnostic liquid that is to be injected. By the piston body being advanced toward a dispensing opening of the container, the liquid is dispensed into a hollow needle. The dispensing can be dosed by controlled displacement of the piston body.

Containers of the aforementioned type are always designed with a round, slender basic shape. A small base area of the piston body has the disadvantage that comparatively high pressures have to be applied to advance the piston body for dispensing the liquid. In containers of the aforementioned type, the liquid to be injected is dosed with the aid of a dosing mechanism that acts directly on the piston body, so that the dose to be injected is made available in the container body itself. This requires a comparatively elaborate dosing and displacement mechanism for preparing the dose and effecting a controlled advance of the piston body.

Injection devices for self-medication by the patient require comparatively small external dimensions of the injection device to ensure optimal transportability. Also desirable is a dosing and displacement mechanism for dosed dispensing of the liquid, which has a comparatively low energy requirement.

DE 196 52 708 A1 discloses a plastic syringe body for medical purposes of the aforementioned type, with a round and slender basic shape. An opening ratio, defined by the ratio of a maximum height of the container body to a maximum distance between side walls of the container body, is considerably greater than one. To be able to apply the comparatively high pressure required for advancing the piston body with minimal force, the base area of the piston is comparatively small, which limits the capacity of the container body and necessitates a large overall height of an injection device receiving the container body.

WO 00/02605 discloses a medical injection device for administration of insulin, with a container of the aforementioned type. A sufficient capacity of the container body necessitates a comparatively large overall height of the injection device, which is disadvantageous especially for self-treatment by patients using portable injection devices.

SUMMARY

An object of the present invention is to provide a container generally of the aforementioned type for storing a product to be injected in such a way that it is suitable for use with a wide variety of dosing and displacement mechanisms. Another object of the present invention is to provide a container from which a product can be dispensed by applying a comparatively low pressure to a piston body. Yet another object of the present invention is to provide a container that can be more safely and reliably exchanged, especially for use in self-medication. Another object of the present invention is to provide an injection device with or in which a container according to the present invention may be used.

In one embodiment, the present invention comprises a container for a substance to be dispensed, the container comprising a container body having one of a lateral wall or lateral walls and a piston in the container body, the piston having a position that determines a maximum amount of substance in the container and being moveable to another position to dispense the substance, wherein a ratio of a maximum height of the container body to a maximum distance between the lateral wall or walls of the container body is approximately 1.25 to 1.0.

In another embodiment, the present invention comprises an injection device for dosed administration of a substance, comprising a container comprising a container body having one of a lateral wall or lateral walls and a piston in the container body, the piston having a position that determines a maximum amount of substance in the container and being moveable to another position to dispense the substance, wherein a ratio of a maximum height of the container body to a maximum distance between the lateral wall or walls of the container body is approximately 1.25 to 1.0, and a displacement mechanism for moving the piston in the container to cause an administration of the substance.

In one embodiment, a container for storing a product to be injected, according to the present invention, comprises a container body having a comparatively small opening ratio, wherein said opening ratio is defined by a quotient H/L, wherein H corresponds to a maximum height of the container body and L corresponds to a maximum distance between side wall or walls of the container body. Thus, the container body according to the present invention comprises a comparatively large base area. An advantage is that, because of the large base area, only comparatively low differential pressures are needed between a piston body and a dispensing opening of the container body to obtain a displacement of the piston body for dispensing the product.

In some embodiments, the aforementioned opening ratio H/L of the container body is at most approximately 1.25, and, in some embodiments it may be at most approximately 1.0. The opening ratio can also be considerably less than 1.0. An advantage is that, as long as the piston body has not yet been inserted into the container body, a comparatively large opening is available, so that the entire inner surface or at least the inner circumferential surface of the side wall or walls of the container body can be coated practically without obstruction, for example by vapor-deposition, sputtering, plasma-coating techniques, sol-gel coating, immersion coating, or such like.

Thus, according to the present invention, a coating can be applied to the surfaces that are relevant for or to the static and/or kinetic friction between container body and piston body to suitably reduce the static and/or kinetic friction between these elements. In this way, the minimum differential pressures required for displacement of the piston body can be still further reduced.

According to a further aspect of the present invention, a container according to the present invention comprises a container body and a piston generally inside the container body, the container having a kinetic friction of approximately 20N between the container body and the piston, wherein an underpressure required for displacement of the piston body is at most approximately 0.2 bar. It is advantageous that, for dispensing a product from the container, the piston can be displaced by a comparatively low pressure. The container according to the invention is therefore also suitable for use in combination with micro diaphragm pumps or other suitable pumps that are distinguished by relatively low pressures, but also by small external dimensions and low energy consumption.

According to a further embodiment, a container according to the present invention comprises a container body and a piston body, wherein there is a static friction of approximately 40N between the container body and the piston body, whereby an underpressure required for displacement of the piston body is at most approximately 0.4 bar. It is advantageous that the piston body for dispensing the product can be displaced by a comparatively low pressure. The container according to the invention is therefore also suitable for use in combination with micro diaphragm pumps that are distinguished by relatively low pressures, but also by small external dimensions and low energy consumption.

According to a further embodiment of the present invention, the aforementioned coating can also be designed to reduce permeation and/or adsorption of gases and/or to lessen a frictional force between the container body and the piston body. As is known, gases, for example oxygen or water vapor, that diffuse through the walls of a container can adversely affect the quality, shelf life and usefulness of a product stored in the container. By applying the aforementioned coating to those surfaces of the container responsible for the diffusion of gases, it is thus also possible to ensure the quality, shelf life and usefulness of the stored product.

Although a container in accordance with the present invention, elements thereof, e.g., the container body, the piston body, etc., can in principle be made from any suitable material or combination of suitable materials. In some embodiments, at least the two aforementioned elements, the container body and the piston, are made from a plastic material, in particular from COC (cyclo-olefin-copolymer). It is advantageous that COC has a relatively low gas permeability and at the same time has good biocompatibility. Moreover, COC is one of the few plastics that can be used for insulin. Another advantage is that said elements can be produced by precise and at the same time low-cost manufacturing processes, for example injection molding. The elements can be manufactured with such precision, and under such hygienic production conditions, as to be able to easily obtain authorizations for medical appliances as required in some countries.

In some preferred embodiments of the present invention, surfaces (e.g., of the container and/or an injection or diffusion device) relevant to the static and/or kinetic friction or to the diffusion of gases are coated with the aid of a low-temperature plasma technique.

Since, according to the present invention, the piston body can be displaced by means of comparatively small differential pressures, the dosing of the product that is to be dispensed can also be accomplished outside the container body, for example by an external pump, for example a micro diaphragm pump. This therefore permits energy-saving microdosing, which is well-suited for portable injection devices and/or for permanent medication of patients. The low static and/or kinetic friction forces that can be achieved according to the present invention are suitable for permanent medication, on account of the resulting low energy required for displacing the piston body.

Although the base area of a container body in accordance with the present invention can in principle be of any desired shape, including circular or elliptical, the base area of one preferred embodiment is polyhedral. Consequently, a free space provided in an injection device for receiving the container can be utilized still more efficiently, so that containers with a greater capacity can be made available while the injection device retains the same external dimensions. In some preferred embodiment, the base area of the container body is substantially rectangular.

In the case of such a rectangular base area, a bevel can be envisaged that shortens two side walls of the container body adjacent to the bevel. The bevel can be suitably detected, for example by optoelectronic or mechanical scanning, so that the shape and position of the container body can easily be determined at all stages, e.g. during production, storage, insertion into an injection device, or disposal. Instead of such a bevel, another suitable marking can of course also be provided on the container body, for example a notch, an optically readable marking, an optical reflector, a microwave reflector, etc.

According to another preferred embodiment of the present invention, the container is designed in two parts and, in addition to the container body and the piston body received in the latter, also comprises a lid for covering the container body. It is advantageous that, by means of the lid, inadvertent displacement of the plug or piston can be avoided, and damage to the container body or piston body or to the liquid stored in the container body can be reliably ruled out. This construction also makes the container easy for patients to handle, for example when exchanging the container in an injection device for self-medication. This is because the container can be treated in the manner of a cartridge or insertable unit (e.g., like a film cartridge), without elements important to the function of the container being accessible from the outside, or without the possibility that the product stored in the container can be contaminated or adulterated. The aforementioned bevel or marking can be used to insert the container into an injection device in a suitable orientation.

In some embodiments, the lid and container body are connected to one another via a lock or suitable interacting locking means, which may comprise a selected number of lock elements. Examples of suitable locks and locking means are catches, hooks, detents, snaps, etc. In some preferred embodiments, the lock comprises projections on the container body or on the lid and corresponding or complementary shaped openings or recesses at corresponding or complementary positions on the lid or on the container body. The firm mechanical connection thus obtained between container body and lid can in principle be releasable, but, in some embodiments, a substantially non-releasable connection is preferred, so that patients cannot accidentally damage elements that are important to the operation of the container or contaminate or adulterate the product stored in the container.

In some preferred embodiments, the aforementioned lock and locking means may be arranged substantially centrally on side wall or walls of the container body and of the lid, respectively, so that the flows of forces are more symmetrical. In some preferred embodiments, the locking means are arranged substantially at the center of a corresponding side wall of the container body or of the lid, respectively, in a substantially point-symmetrical arrangement on the corresponding side wall. Of course, in some embodiments, several locking means can also be formed on a side wall of the container body or of the lid, respectively, in which case expediently a symmetrical arrangement suitable.

According to a further embodiment, the lid has a plurality of recesses, these recesses being arranged at predetermined positions, e.g., in a point-symmetric arrangement, to code for a concentration of the product stored in the container. The recesses are expediently formed on the outer surface of the lid, so that they can be scanned optoelectronically or mechanically from the outside of the container. The recesses can of course also be designed as apertures, for example as through-bores.

Of course, the shape of the recesses can itself also be used for the coding, for example, at least one recess can be rectangular and/or at least one recess can be circular. The aforementioned pattern of points and/or the design of the recesses can also be used in a suitable way for coding of further important parameters of the container, of container elements and/or of the stored product, for example for coding the type of injection device for which the container can be used, the type of product stored, the intended use of the stored product, the expiry date of the container and/or of the stored product, etc.

By way of the aforementioned through-bores provided in the lid, a force from a mechanical displacement mechanism, for example from a spring drive, can also be applied to the piston body via pins that pass through the through-bores for the dispensing of product, without the lid having to be removed from the container body.

For dispensing the product, embodiments of a container in accordance with the present invention comprise a tubular outlet, which is formed near the bottom of the container body, so that practically all of the product is dispensed when the piston body is in a front end position. In some preferred embodiments, the tubular outlet is sealed by a piercing membrane, such that the stored product can be stored hygienically and, after piercing with a hollow needle or the like, can be conveyed to a downstream injection needle or to a downstream mechanism for dispensing and dosing of the product.

In some preferred embodiments, locking means are provided on an outer circumference of the tubular outlet to receive, with a force fit, a closure that is used for closing an outlet opening of the tubular outlet. After the container body has been filled, the closure can be easily attached and locked, for example by snap-fitting. The aforementioned piercing membrane can be provided in the closure.

In some embodiments, for filling with the product to be stored, the container body may be oriented in such a way that the piercing membrane is at the top, and the upright container body can be filled free from bubbles in the manner of conventional ampules.

To ensure that the product can be dispensed substantially completely, in some embodiments, a trough-shaped recess can be provided in a bottom of the container body, which merges into an inlet of the tubular outlet. In the front end position of the piston body, in which the front face of the piston body may abut across a large area against the bottom of the container body, even extremely small residues left in the container body can be conveyed to the dispensing opening of the outlet.

According to a further aspect of the present invention, an injection device is created for dosed administration of a product to be injected, especially a therapeutic or diagnostic liquid. The injection device according to the present invention comprises a container designed in the manner described before, and by a displacement mechanism which is designed to effect dispensing of the product by displacement of the piston body in the container body.

While in ampules such as are conventionally used for injection of therapeutic or diagnostic liquids, an underpressure of about 1 bar, for example, is not sufficient to displace the ampoule plug solely by the prevailing underpressure for dispensing of product, the relatively large cross-sectional area of the piston or piston body according to the present invention reduces the pressure required for displacing. This permits energy-efficient dispensing of the product stored in the container body.

Since, according to embodiments of the present invention, the piston body can be displaced at small differential pressures, it is also possible to use microdosing devices that can generate only relatively small differential pressures. Thus, according to some embodiments of the present invention, a micro diaphragm pump may be used for displacement of the piston body.

By virtue of the low underpressure required for displacement of the piston body in the container body, the pressure at the outlet side of the container body will always be sufficiently great to compensate for pressure losses in downstream areas of the injection device, in particular in hoses and hollow needles.

According to a further embodiment of the present invention, the injection device is designed such that the piston body, in its direction of advance, is acted upon permanently by a force, for example by a compression or tension spring, or by a compressed-air cushion which is at an overpressure and exerts a force on the piston body. In this way, it is possible to ensure an even more energy-efficient operation.

DETAILED DESCRIPTION OF THE DRAWINGS

Figure 1:
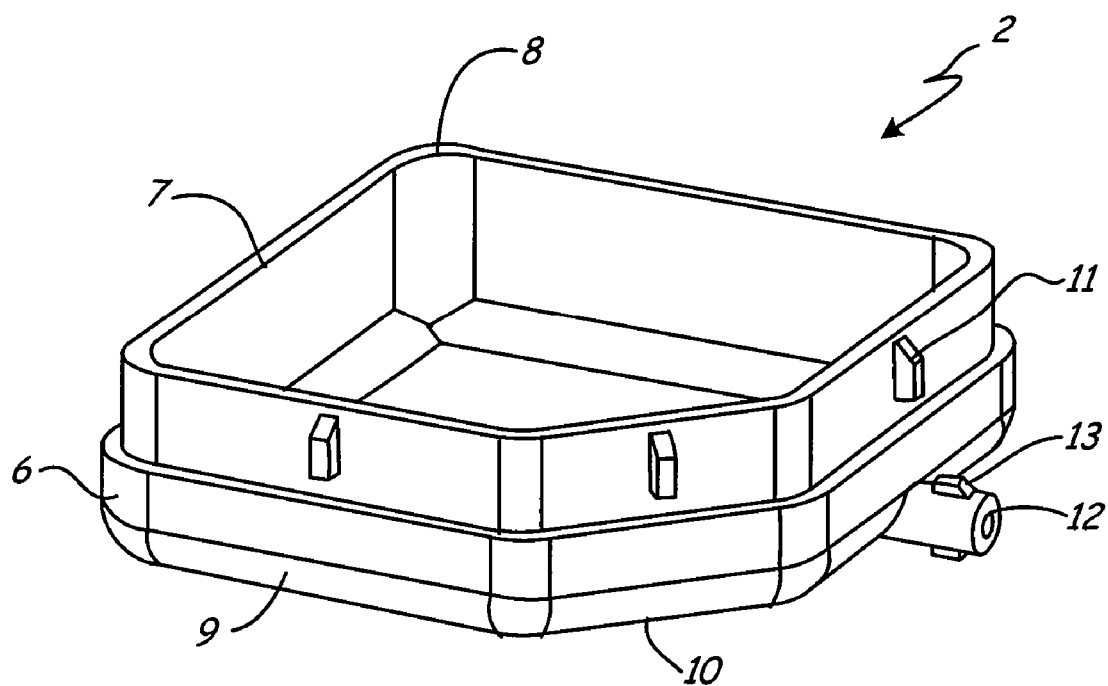
FIG. 1 a perspective view of a container body according to one embodiment of the present invention.

In the figures, identical reference numerals designate identical elements or functional groups, or elements or functional groups that are acting substantially identically.

FIG. 1 shows a perspective view of a container body according to a first embodiment of the present invention. The container body 2 has a substantially rectangular base area, wherein the internal height of the container body 2 is substantially smaller than a maximum distance between the side walls of the container body 2. Therefore, the opening ratio of the container body 2, as defined by the ratio of the maximum internal height of the container body 2 to a maximum distance between side walls of the container body 2, is clearly smaller than one.

The side walls have a stepped design and each comprise a thick-walled portion 6 and a thin-walled portion 7. The difference in wall thickness between the thick-walled portion 6 and the thin-walled portion 7 is adapted to the wall thickness of a lid or cover (see FIG. 6) to be fitted onto the container body 2, in such a way that the outer surfaces of the container thus formed (FIG. 7) are substantially flush with each other.

The side walls of the container body 2 have rounded corner portions 8, so that the inside of the container body 2 can easily be sealed off with the aid of a plug-like piston body (which also may be referred to and/or thought of as a piston, plunger, plug, etc.) (see FIG. 4). As is shown in FIG. 1, the edges of the side walls at the bottom of the container body 2 are beveled, the bevel angle being between about 5 to about 25 degrees.

A side wall 10 of the container body 2 is beveled such that the adjacent side walls of the container body 2 are shortened. As is shown in FIG. 1, at least one substantially rectangular locking lug element 11, serving as locking means, which is beveled on its top side, is formed on each of the side walls, with point symmetry in relation to the thin-walled portions 7. The lug 11 interacts with openings 28 of the lid 4 (FIG. 6) of corresponding configuration, which serve as lock or locking means, such that the lid 4 can be snapped on in a simple way. The lid, when snapped on in this way, cannot be removed again. According to a modified embodiment, the locking lugs 11 can also be elastic, for example with spring elasticity, so that, by pressing in the locking lugs 11 toward the side walls of the container body 2, the snapped-on lid 4 can be removed again.

Formed on the underside of the side wall of the container body 2 adjoining the bevel 10, there is a tubular outlet 12 which, at its front end, has a dispensing opening for dispensing the product stored in the container body 2. The tubular outlet 12 protrudes slightly from the associated side wall of the container body 2, such that a connecting coupling or a hose for connection to a hollow needle or a suction pump can be pushed on.

Secure connection to the hose or connecting coupling is permitted by substantially rectangular locking lugs 13 which serve as locking means and are provided on the outer circumference of the tubular outlet 12. The locking lugs 13 are beveled at one end or at both ends, so that a connecting coupling or hose can easily be pushed over and be held in a loss-proof manner.

Figure 2:
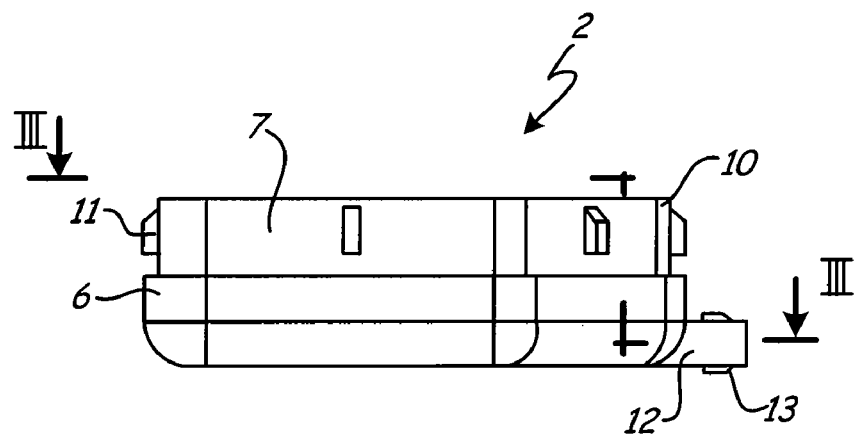
FIG. 2 is a side view of the container body shown in FIG. 1.

FIG. 2 shows a side view of the container body according to FIG. 1. As is shown in FIG. 2, the tubular outlet 12 ends substantially flush with the underside of the container body 2 and an upper edge of the thick-walled portion 6, respectively. As can be taken from FIG. 2, the heights of the thick-walled portion 6 and of the thin-walled portion 7 are substantially identical. The bevel at the lower edge of the thick-walled portion 6 corresponds approximately to about half the height of the thick-walled portion 6.

Figure 3:
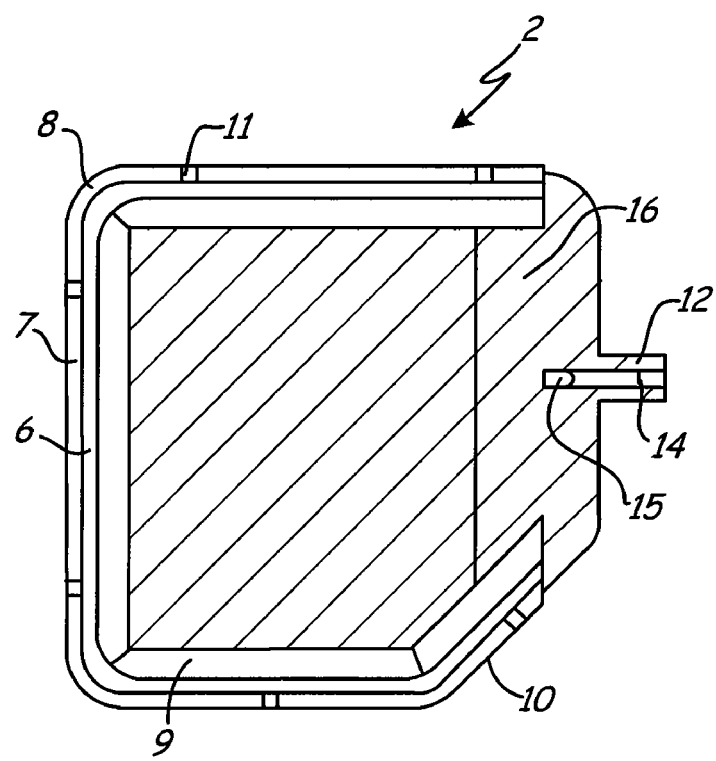
FIG. 3 is a schematic plan view of the container body according to FIG. 2, in partial cross section along the line III-III.

FIG. 3 shows a schematic plan view, in partial section, of the container body 2 according to FIG. 2 along the line III-III. On the right-hand edge of the container body 2, the tubular outlet 12 is formed with a central dispensing opening 14, which is designed as a through-bore and which merges into the interior of the container body 2 via a recess 15 formed in the bottom of the container body 2. As is shown in FIG. 3, the bottom of the container body 2 is surrounded on all sides by bevels 9, so that the interior of the container body can be easily sealed with a piston body (FIG. 4).

Figure 4:
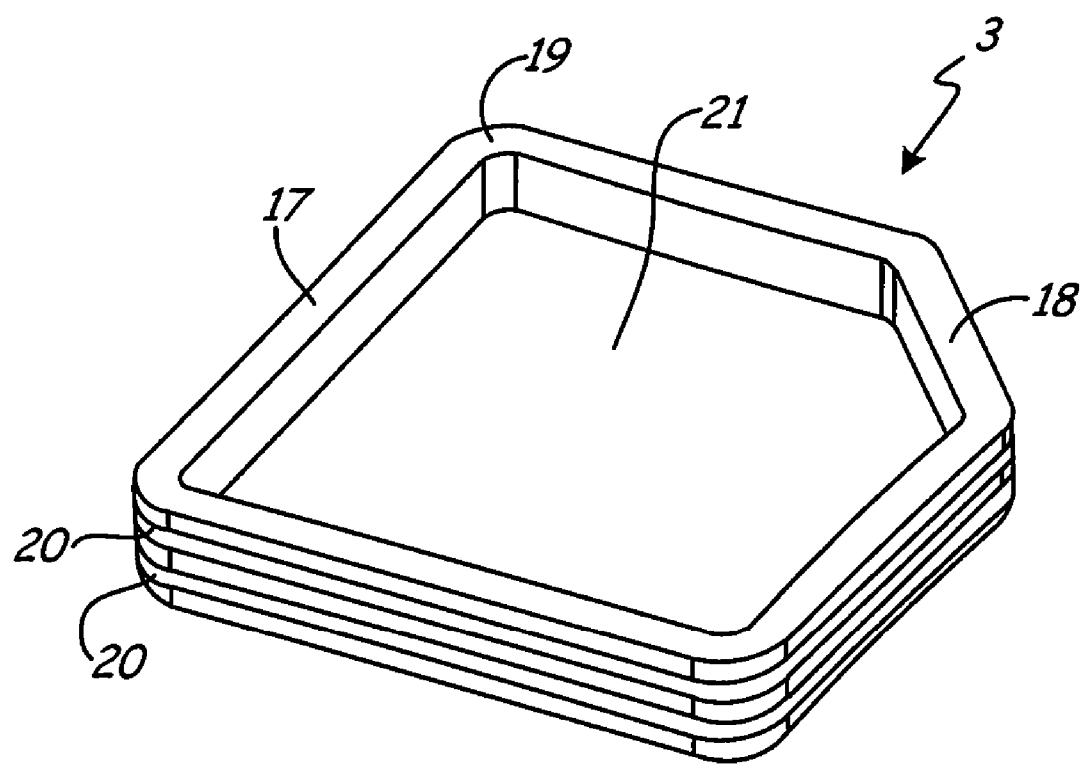
FIG. 4 is a perspective view of a piston body to be received in the container body according to FIG. 1.

FIG. 4 shows a perspective view of a piston body 3 to be received in the container body 2 according to FIG. 1. The outer contour of the plug-like piston 3 is adapted to the inner contour of the container body 2 and is substantially rectangular, with a bevel 18 that shortens two adjacent long sides. The piston body 3 has beveled corner portions 19. The wall thickness of the side walls of the piston body 3 is chosen such to ensure a sufficient inherent stiffness and sealing action.

As is shown in FIG. 4, two circumferential sealing lips 20 functioning as sealing means are formed on the outer circumferential surface of the piston body 3. The lips also may be referred to or thought of a flanges, extensions, etc. They are made of a comparatively soft plastic or rubber material to seal the interior of the container body 2. The sealing lips 20 can be injection-molded onto the outer circumferential surface of the piston body 3. The sealing lips 20 can also be designed as a rectangular plastic or rubber body of circular, elliptic or rectangular profile which is received in a circumferential recess formed on the outer circumferential surface of the piston body 3. Alternatively, the sealing means 20 can also be injection-molded onto the inner circumferential surface of the container body 2 or designed in the aforementioned manner, and the outer circumferential surface of the piston body 3 can be made substantially smooth. According to FIG. 4, the piston body 3 is substantially trough-shaped. Of course, the piston body 3 can also be designed as a flat plate body. According to FIG. 4, two sealing lips 20 are formed lying vertically one above the other. Any liquid passing through the sealing gap between the lower sealing lip 20 and the inner circumferential surface of the container body 2 can thus be retained in the gap between the lower and the upper sealing lips 20. Of course, it is also possible to provide one, three or more sealing lips 20.

Figure 5:
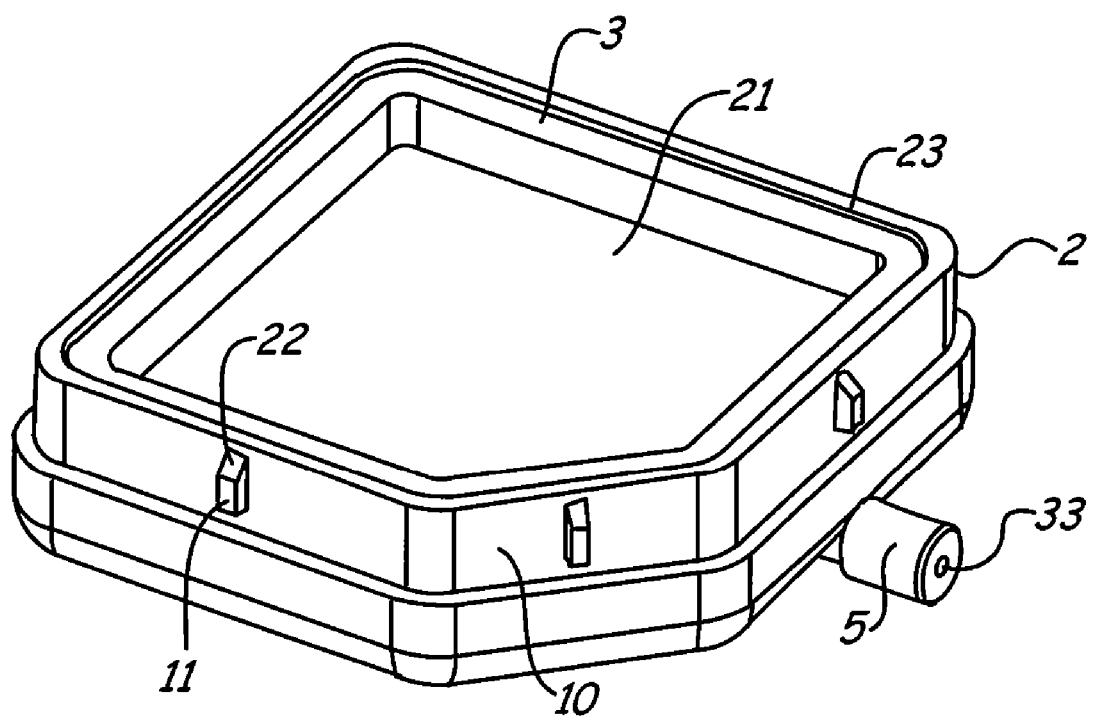
FIG. 5 is a perspective view of the container body shown in FIG. 1, with the piston body shown in FIG. 4 received therein.

FIG. 5 shows a perspective view of the container body 2 according to FIG. 1, with the piston body according to FIG. 4 received in it. A closure 5 is snapped onto the front end of the tubular outlet 12, which has a piercing membrane 33 for closing the dispensing opening of the tubular outlet 12. After the piercing membrane 33 has been pierced by means of a hollow needle or the like, product from the container body 2 can be dispensed by moving or advancing the piston body 3 toward the bottom of the container body 2 in a dispensing movement.

To fill the container body 2, the piston body 3 is brought to the rear end position shown in FIG. 5, which position determines a maximum filling of the container body 2. The container body 2 is expediently oriented upright for filling, such that the tubular outlet 12 protrudes upward from the side walls of the container body 2, and the container body 2 rests on the side wall lying opposite the tubular outlet 12. For orientation of the container body 2, the bevel 10 can be scanned by an optoelectronic or mechanical sensor device.

In this orientation, liquid can be introduced through the dispensing opening 14 of the tubular outlet 12 into the space between the underside of the piston body 3 and the bottom of the container body 2. For this purpose, the liquid can be introduced via a hollow needle whose external diameter is smaller than the internal diameter of the dispensing opening 14 of the tubular outlet 12. The dispensing opening 14 is then closed by snapping-on of the closure 5 with the piercing membrane 33.

Figure 6:
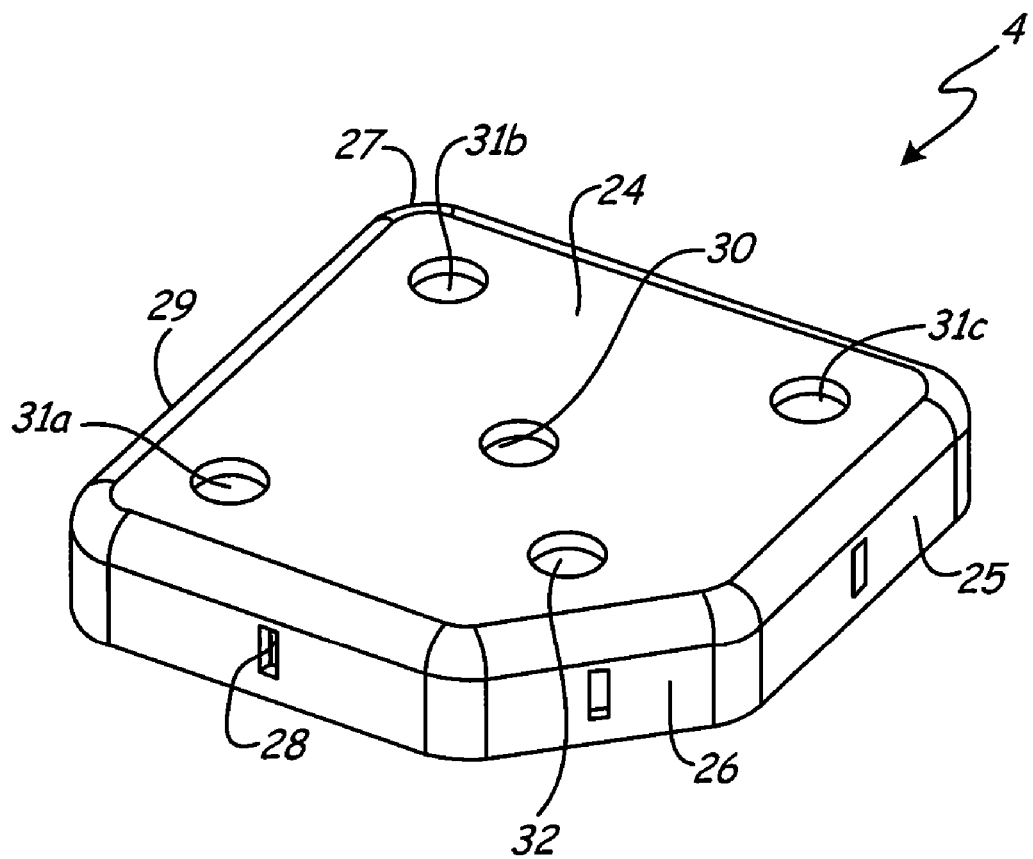
FIG. 6 is a perspective view of an embodiment of a lid of the container body shown in FIG. 1.

FIG. 6 shows a perspective view of a lid 4 for the container body 2 according to FIG. 1. The shape of the lid 4 is substantially rectangular and is substantially identical to that of the container body 2 according to FIG. 1. The lid 4 comprises a top side 24 and side walls 25 projecting substantially vertically from the top side 24. The transition area between the side walls 25 and the top side 24 is beveled. One of the side walls 25 forms a bevel 26 such that the adjacent side walls 25 are shortened. As is shown in FIG. 6, at least one recess 28 serving as a lock or locking means is formed in each case on the side walls 25 and on the bevel 26, which interact with the correspondingly shaped locking lugs 11 (FIG. 1) on the side walls of the container body 2, such that the lid 4 can be snapped onto the container body 2 and can be held there in a loss-proof manner. As can be seen in FIG. 6, the recesses 28 are formed substantially with point symmetry on the rectilinearly projecting side walls 25 and the bevel 26.

A plurality of recesses 30, 31a-c and 32 designed as through-bores are formed on the top side 24 of the lid 4. The through-bore 30 is formed centrally on the top side 24. The through-bores 31a-c are formed in a point-symmetric arrangement in the respective corners of the lid 4. The through-bore 32 lying nearest to the bevel 26 is arranged closer to the central through-bore 30 than is the through-bore 31b lying diametrically opposite it. Together, the recesses formed as through-bores form a patterns of points that can be scanned optoelectronically or mechanically and can be used for a coding. According to the present invention, the concentration of the liquid stored in the container may be coded with the aid of the pattern of points. Of course, the pattern of points can also be used to code other parameters and properties of the stored liquid, of the container, of the container body and/or the piston body, for example the nature of the stored liquid, the manufacturer, the type of injection device to be used, the content of the container, and such like.

Figure 7:
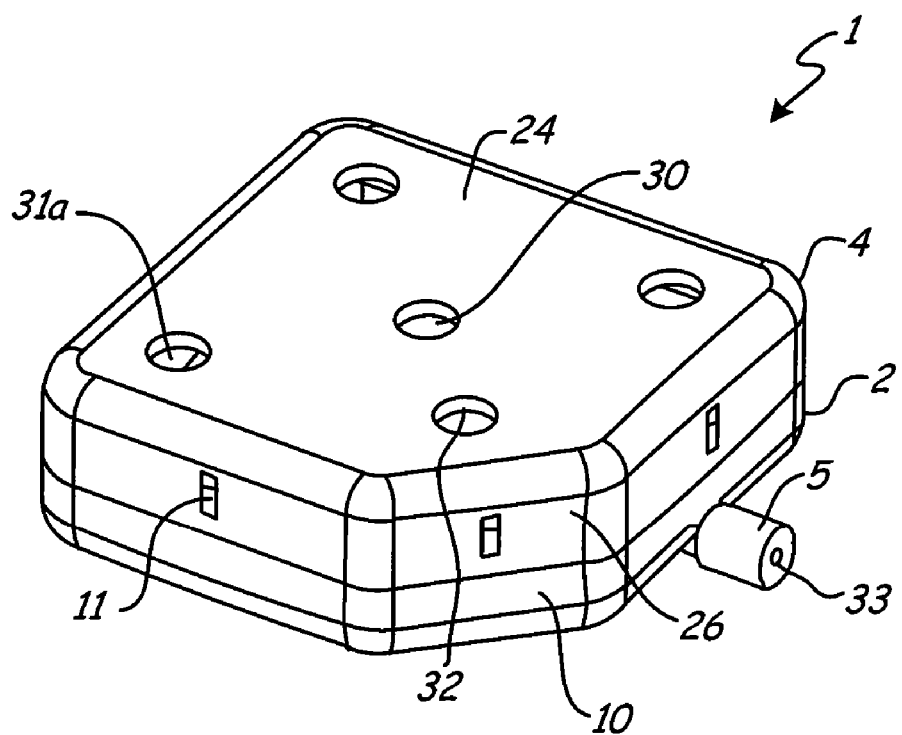
FIG. 7 is a perspective view of a container according to the present invention with the container body of FIG. 1 and the lid of FIG. 5.

FIG. 7 shows a perspective view of a container 1 according to the present invention with the container body 2 according to FIG. 1 and the lid 4 according to FIG. 5. According to FIG. 7, the lid 4 is snapped onto the container body 2 in the rear end position of the piston body 3 shown in FIG. 5, so that the locking lugs 11 engage in the locking apertures of corresponding design formed in the side walls and in the bevel 26 of the lid 4. In this configuration the container 1 may be stored and supplied. In this configuration, the piston body 3 is practically inaccessible from the outside of the container 1, so that an inadvertent dispensing of product can be avoided. Moreover, important properties of the stored product, of the container and such like are clearly indicated by means of the coding which is defined by the pattern of points on the top side 24 of the lid 4 and which can be scanned from outside the container 1. Moreover, an installation position of the container 1 can be clearly defined by the bevel 10. The container can thus reliably and safely be exchanged.

Figure 8:
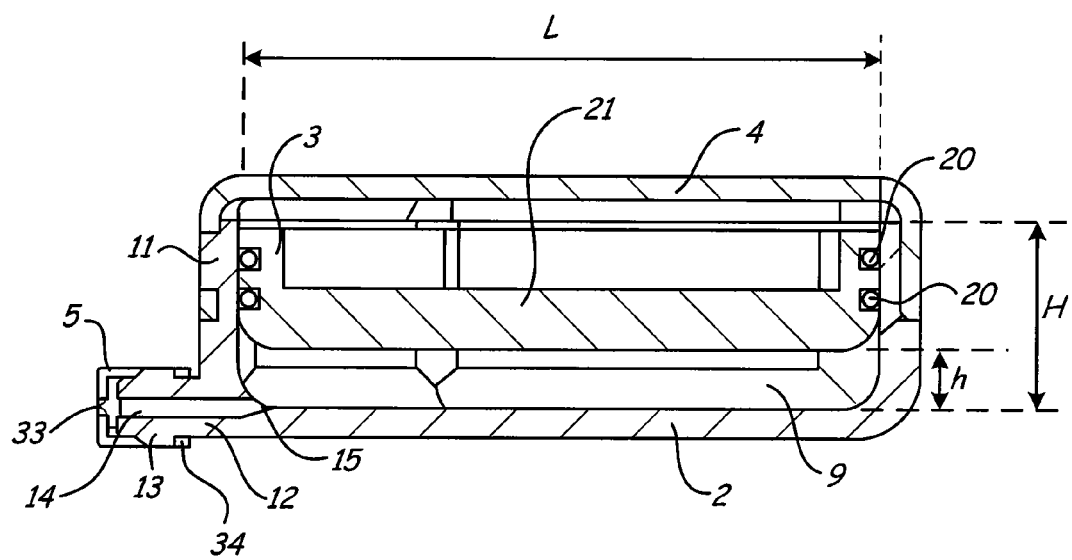
FIG. 8 is a cross section through the container shown in FIG. 7.

FIG. 8 shows a cross section through the container according to FIG. 7. As is shown in FIG. 8, in the rear end position of the piston body 3, the top side of the container body 2 protrudes slightly above the side walls of the piston body 3, so that an at all times constant maximum filling level can be defined also when filling the container body 2. The maximum distance between the inner circumferential surfaces of the side walls of the container body 2 is L. The maximum internal height of the container body 2 is H, wherein the beveled edges at the bottom of the container body 2 have a height h. As can be taken immediately from FIG. 8, an opening ratio of the container 1, which is defined by the ratio H/L, is very much smaller than one. Starting from an opening ratio of approximately 1.25, coating or applying a coating to the inner circumferential surfaces of the container body 2 is easily possible. According to some embodiments of the present invention, opening ratios of less than or equal to 1.0 are preferably used, and, in some embodiments, the opening ratio may be very much smaller than one.

According to the present invention, the base area of the container body 2 and the properties of the inner circumferential surfaces of the container body 2 are chosen such that, with a kinetic friction of 20N (ISO standard) between the container body 2 and the piston body 3, an underpressure required for displacement of the piston body 3 is at most approximately 0.2 bar.

Moreover, according to some embodiments of the present invention, the base area of the container body 2 and the properties of the inner circumferential surfaces of the container body 2 are chosen such that, with a static friction of 40N (ISO standard) between the container body 2 and the piston body 3, an underpressure required for displacement of the piston body 3 is at most approximately 0.4 bar.

Figure 9:
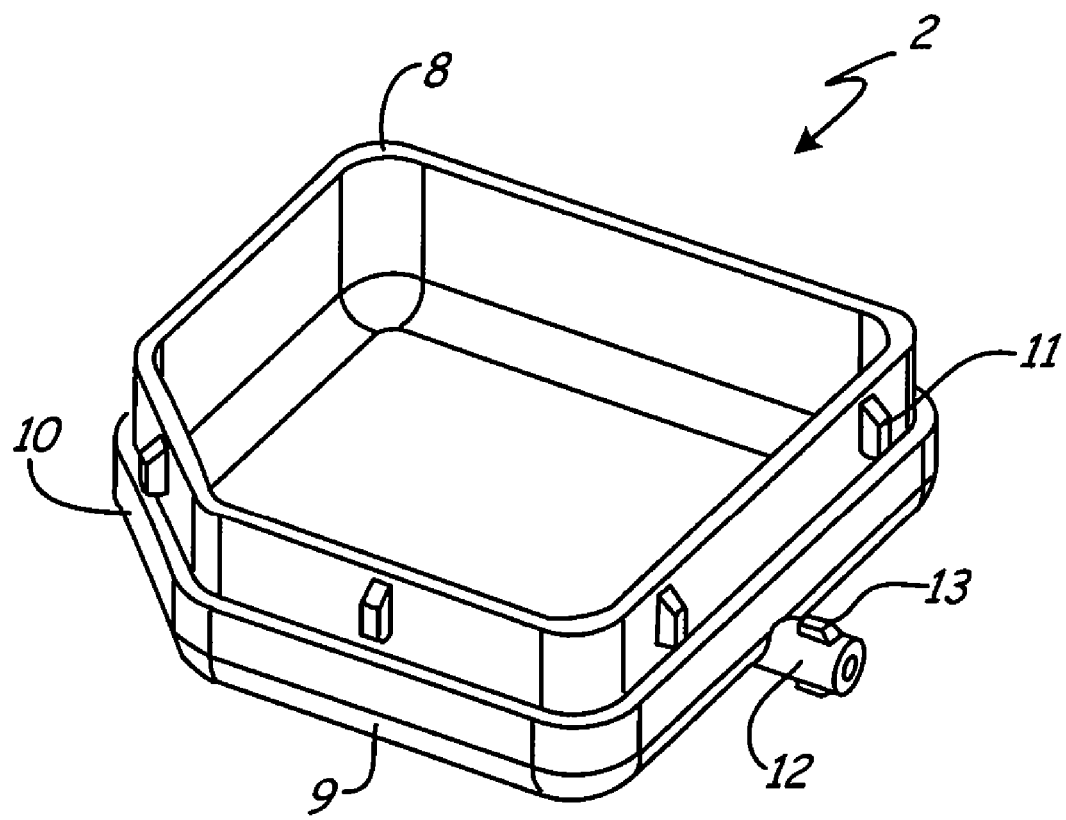
FIG. 9 is a perspective view of a modified container body.

FIG. 9 shows a perspective view of a modified container body according to FIG. 1. According to FIG. 9, the bevel 10 is not designed adjacent to the side wall of the container body 2 comprising the tubular outlet 12. The bevel 10 can be scanned optoelectronically or mechanically in order to indicate the orientation of the container body 2.

Figure 10:
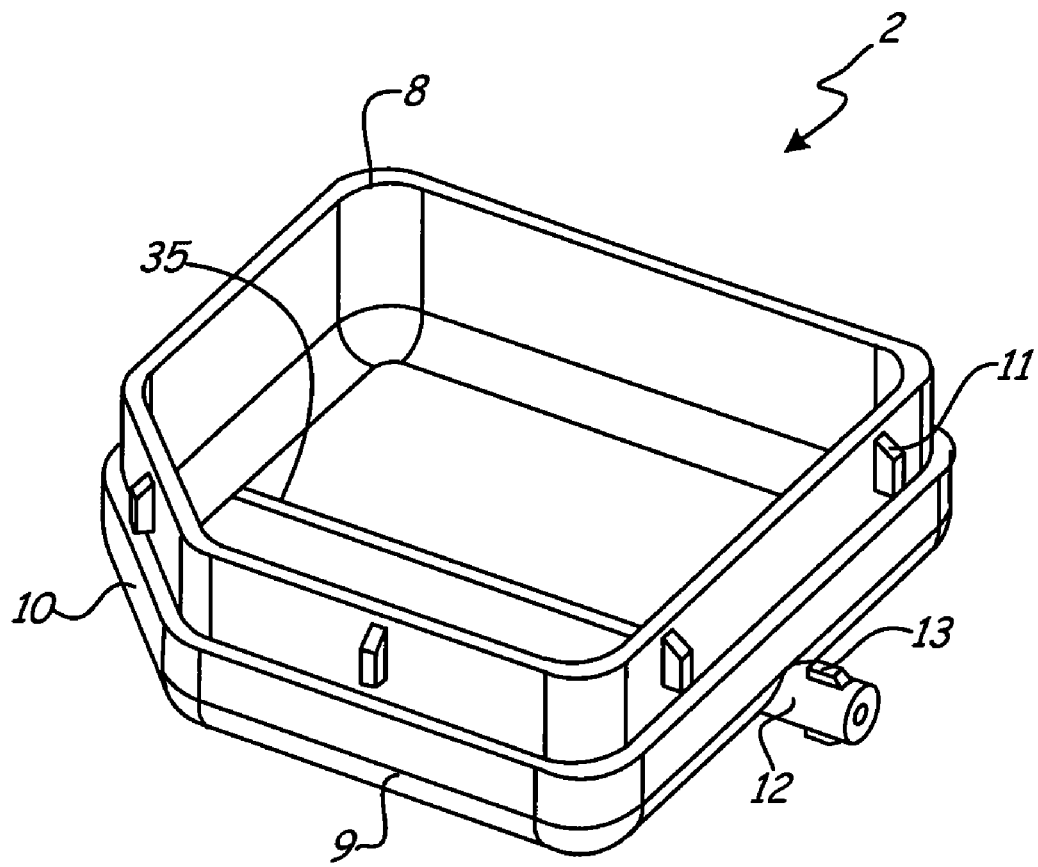
FIG. 10 is a perspective view of a container body according to another embodiment of the present invention.

FIG. 10 shows a perspective view of a container body according to a second embodiment of the present invention. According to FIG. 10, a trough-shaped recess or longitudinal groove 35 is formed in the bottom of the container body 2, which merges into the dispensing opening, designed as through-bore, of the tubular outlet 12. When the piston body (not shown in FIG. 10) in its front end position practically completely rests against the bottom of the container body 2, even very small residual amounts of the stored product left in the container body 2 are reliably conveyed to the dispensing opening.

Figure 11:
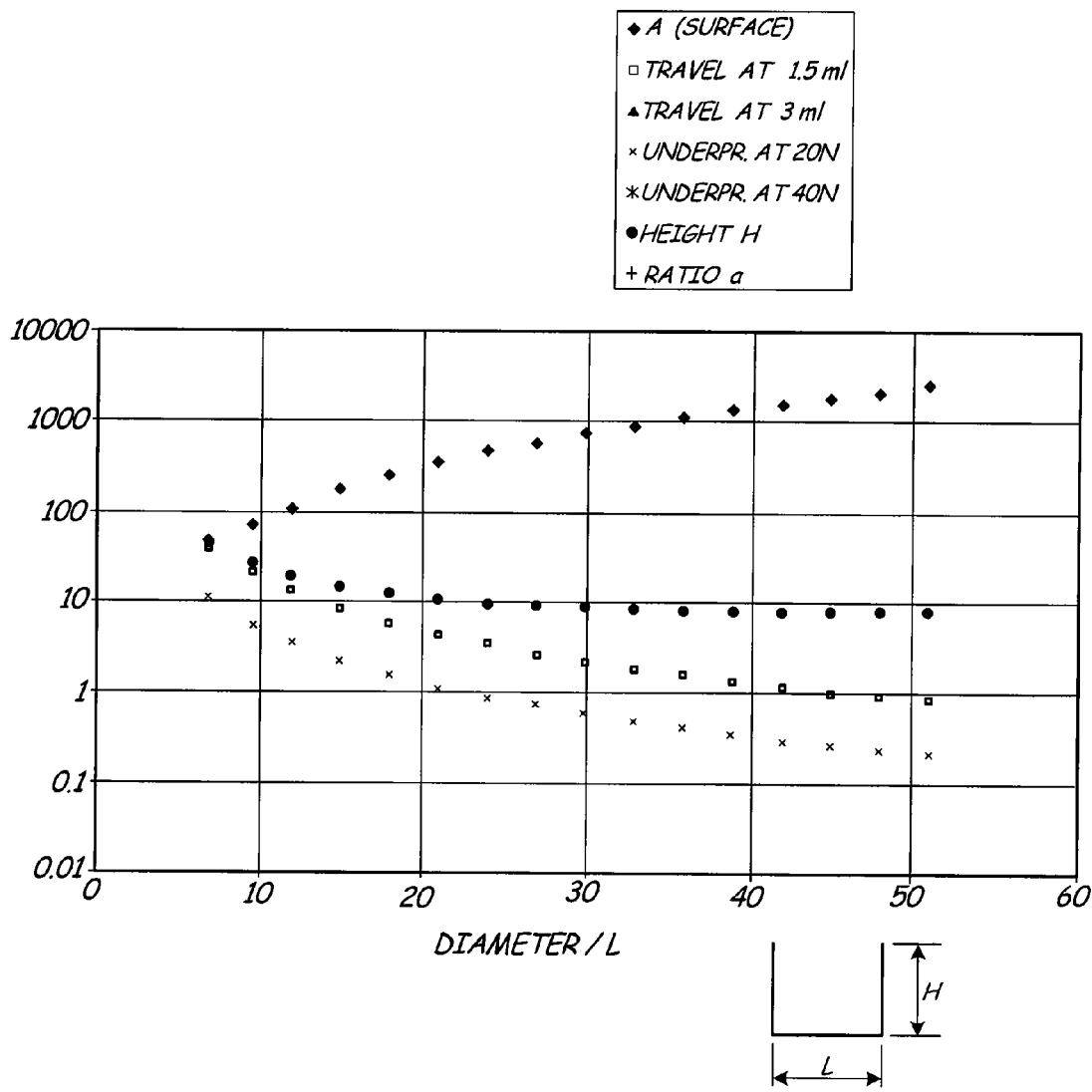
FIG. 11 is a schematic representation of pressures applied to displace the piston body in one embodiment of a container according to the present invention.

FIG. 11 shows a schematic, semi-logarithmic representation of the pressures that have to be applied to displace the piston body in the container according to the present invention, together with other relevant properties of the container.

According to the sequence from top to bottom in the caption of FIG. 11 it shows date values as follows:
- by diamonds—the total base area of the container according to the present invention, assuming a quadratic cross section of the container;
- by dark squares—the maximum travel of the piston body required for dispensing a total of 1.5 ml;
- by light triangles—the maximum travel of the piston body required for dispensing a total of 3.0 ml;
- by x—the underpressure required for displacement of the piston body, assuming a kinetic friction of 20N between the piston body and the container body;
- by a star—the underpressure required for displacement of the piston body, assuming a static friction of 40N between the piston body and the container body;
- by the dark circles—the total height H of the container body required for achieving a constant capacity of the container body; and
- by the plus signs—the respective opening ratio a=H/L, wherein according to the schematic view down right in the FIG. 11, H corresponds to a maximum height of the container body and L corresponds to a maximum distance between side walls of the container body.

In some preferred embodiments, the aforementioned container body and its elements, in particular the piston body and the sealing means, are produced by injection molding from a plastic material. COC (cyclo-olefin-copolymer), which is one of the few plastics that is suitable for storing insulin, has proven expedient as the material. the bevel of the container or by an optical or mechanical marking provided on the housing of the container.

To move the piston body forward, in some embodiments, a micro diaphragm pump may be used (such pumps and the like may be known by other names or terms of art). Examples of suitable pumps are disclosed in DE 4 402 119 A1 or DE 197 37 173 A1, for example, the contents of which are hereby expressly incorporated by way of reference in the present application, in particular with regard to the structure and the mode of operation of the micro diaphragm pumps.

As is known, micro diaphragm pumps of the aforementioned type can be used to generate, in an energy-saving manner, relatively low differential pressures in the range of approximately 1.5 bar. Micro diaphragm pumps of the aforementioned type are further distinguished by taking up a comparatively small amount of space, so that in combination with the container according to the invention, which likewise requires a comparatively small base area, relatively small injection devices can be formed which can be more easily transported or carried around by the patient and which have a low energy requirement. Such an injection device is well-suited for permanent administration of microdoses of insulin for self-medication of patients with diabetes.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A container for a substance to be dispensed, the container comprising
   a container body having one of a lateral wall or lateral walls and a piston in the container body, the lateral wall or lateral walls and the piston at least partially defining a chamber within the container body for accommodating a substance, the piston having a position that determines a maximum volume of the chamber and being moveable to another position to dispense the substance,
   wherein a ratio of a maximum height of the chamber to a maximum distance between the lateral wall or walls of the container body is approximately 1.25 to 1.0.

2. The container according to claim 1, wherein the container body comprises a base that is polygonal and further defines the chamber.

3. The container according to claim 2, wherein the container body comprises an inner surface carrying a coating to reduce at least one of permeation or adsorption of gases and a frictional force between the container body and the piston.

4. The container according to claim 3, wherein an inner surface of at least one of the container body or the container body and a surface of the piston body is provided with a coating to reduce at least one of permeation or adsorption of gases or a frictional force between the container body and the piston body.

5. An injection device for dosed administration of a substance, comprising:
   a container comprising a container body having one of a lateral wall or lateral walls and a piston in the container body, the lateral wall or lateral walls and the piston at least partially defining a chamber within the container body for accommodating a substance, the piston sealingly abutting the lateral wall or the lateral walls and having a position that determines a maximum volume of the chamber and being moveable to another position to dispense the substance, wherein a ratio of a maximum height of the chamber to a maximum distance between the lateral wall or walls of the container body is less than approximately 1.25; and
   a displacement mechanism for moving the piston in the container to cause an administration of the substance.

6. A container for storing a product to be injected, for example a therapeutic or diagnostic liquid, said container comprising:
   a container body comprising side walls; and
   a piston body arranged in the container body in a sliding manner, wherein the side walls and the piston body at least partially define a chamber within the container body for storing the product, wherein to dispense the product, the piston body is displaced between a rear end position which determines a maximum volume of the chamber and a front end position; wherein
   an opening ratio of a maximum height of the chamber to a maximum distance between the side walls is at most approximately 1.25; and wherein
   an inner surface of the side walls is provided with a coating to reduce a frictional force between the container body and the piston body.

7. The container according to claim 6, wherein the opening ratio is at most approximately 1.0.

8. The container according to claim 6, wherein a kinetic friction between the container body and the piston body is approximately 20N, and wherein an underpressure required for displacement of the piston body is at most approximately 0.2 bar.

9. The container according to claim 6, wherein a static friction between the container body and the piston body is approximately 40N, and wherein an underpressure required for displacement of the piston body is at most approximately 0.4 bar.

10. A container for storing a product to be injected, in particular a therapeutic or diagnostic liquid, comprising:
    a container body comprising side walls; and
    a piston body arranged in the container body in a sliding manner, wherein the side walls and the piston body at least partially define a chamber within the container body for storing the product, wherein to dispense the product, can be the piston body is displaced between a rear end position which determines a maximum volume of the chamber filling and a front end position; wherein
    the container body is designed such that, with a kinetic friction of 20N between the container body and the piston body, an underpressure required for displacement of the piston body is at most approximately 0.2 bar.

11. The container according to claim 10, wherein, with a static friction of 40N between the container body and the piston body, an under pressure required for displacement of the piston body is at most approximately 0.4 bar.

12. The container according to claim 10, wherein an inner surface of at least one of the container body or the container body and a surface of the piston body is provided with a coating to reduce at least one of permeation or adsorption of gases or a frictional force between the container body and the piston body.

13. The container according to claim 10, wherein at least the container body is made of cyclo-olefin-copolymer.

14. The container according to claim 10, further comprising a base area that is rectangular.

15. The container according to claim 14, wherein the container body comprises two side walls and a bevel that shortens the two side walls.

16. The container according to claim 10, further comprising a lid for covering the container body, wherein the lid is connected to the container body via a lock.

17. The container according to claim 16, wherein the lock comprises complementary elements arranged substantially centrally on the container body and the lid.

18. The container according to claim 16, wherein the lid comprises a number of recesses at predetermined positions to code for a concentration of the product.

19. The container according to claim 18, wherein the recesses are in a point-symmetrical arrangement.

20. The container according to claim 10, further comprising a tubular outlet for dispensing the product.

21. The container according to claim 20, wherein the tubular outlet is sealed by a piercing membrane.

22. The container according to claim 21, further comprising locking means on an outer circumference of the tubular outlet for receiving, by a force fit, a closure for closing an outlet opening of the tubular outlet.

23. The container according to claim 22, wherein the container body further comprises a bottom defining a trough-shaped recess which merges into an inlet of the tubular outlet.

24. An injection device for the dosed administration of a product, in particular a therapeutic or diagnostic liquid, comprising;

a container comprising a container body and a piston body arranged in the container body such that the piston body is slidable relative to sidewalls of in the container body, wherein the side walls and the piston body at least partially define a chamber within the container body for storing the product, the piston having a rear end position that determines a maximum volume of the chamber and being moveable between the rear end position and a front end position to dispense a maximum amount of produc, wherein an opening ratio of a maximum height of the chamber to a maximum distance between the side walls of the container body is about 1.25 or less; and a displacement mechanism for displacing the piston body in the container body to administer a dose of the product.

25. The injection device according to claim 24, wherein the displacement mechanism comprises a micro diaphragm pump.

26. The injection device according to claim 25, wherein the displacement of the piston body is in a single direction.

27. The injection device according to claim 24, wherein the container body is designed such that, with a kinetic friction of 20N between the container body and the piston body, an underpressure required for displacement of the piston body is at most approximately 0.2 bar.

28. The injection device according to claim 24, further comprising an outlet for dispensing the product, wherein the outlet extends in a direction that is different than an advancing direction of the piston body.

* * * * *

UNITED STATES PATENT AND TRADEMARK OFFICE
CERTIFICATE OF CORRECTION

| | | |
|---|---|---|
| PATENT NO. | : 7,914,500 B2 | Page 1 of 1 |
| APPLICATION NO. | : 11/564982 | |
| DATED | : March 29, 2011 | |
| INVENTOR(S) | : Simone Garner-Geiser, Rudolf Zihlmann and Hanspeter Heiniger | |

It is certified that error appears in the above-identified patent and that said Letters Patent is hereby corrected as shown below:

Col. 12, Line 49, "can be the piston body" should read -- the piston body --

Col. 12, Line 51, "of the chamber filling and" should read -- of the chamber and --

Col. 14, Line 3, "to sidewalls of in the" should read -- to sidewalls of the --

Col. 14, Line 9/10, "amount of produc" should read -- amount of product --

Signed and Sealed this

Twenty-seventh Day of September, 2011

David J. Kappos
*Director of the United States Patent and Trademark Office*